United States Patent
Messerly et al.

(10) Patent No.: US 8,348,880 B2
(45) Date of Patent: Jan. 8, 2013

(54) ULTRASONIC SURGICAL INSTRUMENT INCORPORATING FLUID MANAGEMENT

(75) Inventors: Jeffrey D. Messerly, Cincinnati, OH (US); Craig N. Faller, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1733 days.

(21) Appl. No.: 10/659,416

(22) Filed: Sep. 10, 2003

(65) Prior Publication Data
US 2005/0049546 A1    Mar. 3, 2005

Related U.S. Application Data

(63) Continuation-in-part of application No. 09/826,070, filed on Apr. 4, 2001, now abandoned.

(60) Provisional application No. 60/412,845, filed on Sep. 23, 2002.

(51) Int. Cl.
*A61B 17/20* (2006.01)

(52) U.S. Cl. ........................................ 604/22

(58) Field of Classification Search ............. 604/22; 600/437, 439; 606/169
See application file for complete search history.

(56) References Cited

U.S. PATENT DOCUMENTS

| | | | |
|---|---|---|---|
| 3,076,904 A | 2/1963 | Kleesattel et al. | |
| 4,136,700 A | 1/1979 | Broadwin et al. | |
| 5,275,607 A * | 1/1994 | Lo et al. ................ | 606/169 |
| 5,957,936 A | 9/1999 | Yoon et al. | |
| 6,589,200 B1 * | 7/2003 | Schwemberger et al. ...... | 604/22 |
| 2002/0077550 A1 | 6/2002 | Rabiner et al. | |

FOREIGN PATENT DOCUMENTS

| | | |
|---|---|---|
| JP | 7178110 A | 7/1995 |
| JP | 2001178734 A | 7/2001 |
| WO | WO 01/24714 A1 | 4/2001 |
| WO | WO 02/094103 A | 11/2002 |

OTHER PUBLICATIONS

International Search Report dated Jan. 6, 2005 for corresponding patent application, International Patent Application No. PCT/US03/29474.

Written Opinion dated Nov. 3, 2005 for corresponding patent application, International Patent Application No. PCT/US03/29474.

* cited by examiner

*Primary Examiner* — Theodore J. Stigell
*Assistant Examiner* — Deanna K Hall
(74) *Attorney, Agent, or Firm* — Verne E. Kreger, Jr.

(57) ABSTRACT

Disclosed is an ultrasonic surgical device having a distally/proximally movable fluid management system consisting of single lumen or multiple lumens. The invention provides for the delivery of irrigation fluid or the removal of fluid, debris or vapor from the tissue-effecting portion of the blade while minimizing the loading on the blade. The blades of the surgical device, when excited at a natural blade system frequency, will have modal shapes characterized by longitudinal, transverse and/or torsional motion and will have nodal locations for these motions at positions along the tissue effecting length of the blade. The instrument is designed to allow for the fluid management system to be positioned at one or more motion nodes to facilitate efficient removal of tissue or fluid, which tends to accumulate at such nodes of the ultrasonic surgical blades.

18 Claims, 9 Drawing Sheets

ULTRASONIC SURGICAL INSTRUMENT INCORPORATING FLUID MANAGEMENT

CROSS REFERENCE TO RELATED APPLICATIONS

The present application is a continuation-in-part of U.S. patent application Ser. No. 09/826,070 filed on Apr. 4, 2001 now abandoned entitled "Blades with Functional Balance Asymmetries for Use with Ultrasonic Surgical Instruments" and further claims the priority benefit of U.S. provisional patent application Ser. No. 60/412,845, filed on Sep. 23, 2002, both of which are incorporated by reference in their entirety herein.

FIELD OF THE INVENTION

The present invention relates to an ultrasonic surgical instrument for cutting, coagulating, grasping and blunt-dissecting tissue, and particularly relates to an ultrasonic surgical instrument having a port or lumen for providing fluid, vapor and/or debris management, such as, suction or irrigation to the surgical site. The present invention is, in one embodiment, specifically adapted for endoscopic surgery, although it has other medical applications as well.

BACKGROUND OF THE INVENTION

The prior art often features a suction system located at the distal end of an ultrasonic phacoemulsifier. This allows for suction/irrigation, but a problem exists in that the fluid suctioned or expelled from the ultrasonic phacoemulsifier is heated due to its direct contact with the ultrasonic blade. Fluids that come in direct contact with the ultrasonic blade cause a substantial heat reduction making the cauterization feature of the instrument less effective. The fluid in direct contact with the ultrasonic blade causes a decrease in the available transmitted ultrasonic energy, that is, the fluid dampens or loads the blade system requiring more input power to achieve the desired tissue effect. In addition, the tissue and/or fluids being transmitted through the blade cavity tend to accumulate at the nodes of the blade. This accumulation creates a blockage within the blade, which results in a reduced flow situation and even more power loss due to blade loading.

There is a need for an ultrasonic surgical device with suction and/or irrigation capabilities in which the suction/irrigation does not increase (due to, for example, loading of the blade system due to a collection of debris) or decrease (due to, for example, convective cooling) the heat emissions of the blade nor decrease the net power of the blade available to do work. A need is also present for an ultrasonic surgical device to effectively eliminate debris, which is known to collect at or near the nodes (longitudinal, torsional and/or transverse-modes or motion) of ultrasonic blades. In addition, a need is present to eliminate vapor from the ultrasonic transections to allow for increased visibility for the clinical user.

The present invention addresses the deficiencies of the prior art and provides an ultrasonic surgical instrument that is useful in both open and endoscopic surgical applications in addition to robotic-assisted surgeries.

BRIEF SUMMARY OF THE INVENTION

The present invention provides for an ultrasonic surgical device having a distally/proximally movable fluid management system consisting of single lumen or multiple lumens, which is positioned so as to minimally contact the ultrasonic blade. The invention provides for means of controlled delivery/removal of fluids, debris or vapor to and/or from the tissue effecting portion of the blade while minimizing the loading on the blade. The blades in the preferred embodiment are non-axisymmetric in at least one plane and have modal shapes at a given natural excitation frequency characterized by longitudinal, transverse, and/or torsional motion patterns where at least one nodal point along the tissue-effecting portion of the blade exists and is defined by a minimum (approximately zero) vibratory motion of the blade in a direction and at least one antinodal position exists along the tissue effecting portion (for example, at the distal tip) where the motion in the same direction is a maximum. This invention can also be used with axisymmetric blades that propagate vibratory motion in any of the aforementioned forms (longitudinal, transverse, and torsional) or combinations thereof wherein at least one motion nodal point is available for effecting tissue. The preferred instrument is designed to allow for the fluid management system to be positioned at one or more transverse (mode or motion) node to facilitate efficient removal of tissue or fluid, which tends to accumulate at such nodes of non-axisymmetric ultrasonic surgical blades.

It is known that during ultrasonic surgical procedures fluid and tissue accumulates at the nodes (longitudinal, transverse, and torsional-modes or motion). The present invention takes advantage of this phenomenon by utilizing a movable single lumen or movable multiple lumens, which may be placed for suction/irrigation at any of the nodes contained within the working portion of the end-effector. It may also be beneficial for the surgeon to have the ability to position the lumen/lumens anywhere along the working portion of the end-effector. Less suction is therefore required to remove the tissue or particles that have already accumulated near the nodal locations.

The present invention has the advantage of having the movable suction/irrigation lumen/lumens located away from the ultrasonic blade. In the prior art, instruments that have a suction system, an irrigation system, or both, in contact with the ultrasonic blade, have several disadvantages as earlier discussed. By locating the movable suction/irrigation lumen/lumens away from the blade, the coagulating temperature of the blade is not decreased and the unpredictable temperature increase of the blade that are due to tissue accumulation at the transverse (mode or motion) nodes of the blade are eliminated. In the present invention, the ultrasonic blades may also be solid as opposed to the necessary hollow blades seen in the prior art. This solid construction allows for better blade strength and allows more versatility of construction and shape.

The movable suction/irrigation lumen/lumens allows physicians to suction/irrigate at the most optimal location. Various blades will have different nodal (longitudinal, transverse, and torsional-mode or motion) locations due to the abundance of blade lengths, operating frequencies, materials, and geometry that affect the characteristic mode shape(s) of the blade that will be excited during use. A movable suction/irrigation lumen/lumens enables physicians to locate the suction/irrigation system at the desired location (nodal or otherwise), wherever that may be on a given blade.

The present invention also features the advantage of a channel located in the tissue-effecting portion of the ultrasonic blade. Fluid and tissue, which have a tendency to congregate at the nodal location, are more easily removed because the channel prevents collected particles from escaping from the suction device. The channel may also be used to direct irrigation fluid to the surgical site. Additionally, the channel may come in contact with the lumen/lumens in order to provide support or partially constrain the lumen. The channel may come in a variety of embodiments such as a spoon shape, wide curve, etc. The lumen may also be moved proximally in order to evacuate aerosol and/or vapor from the surgical site during the procedure.

The lumen/lumens may also be positioned to deliver irrigation through the device. Irrigation is, at times, beneficial to remove tissue and/or blood from the device when the blade is active. It is also beneficial to deliver irrigation to the surgical site in order to improve the visualization or clean the site in question. It makes sense that the lumen/lumens would be movable infinitely along the working portion of the end-effector. In the case of the surgical site irrigation, it may be beneficial to allow movement of the lumen/lumens beyond the distal tip of the blade.

BRIEF DESCRIPTION OF THE FIGURES

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, the surgical instrument and blade configurations disclosed below are illustrative only and not meant to limit the scope or application of the invention. Furthermore, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, methods, etc. can be combined with or are descriptive of any one or more of the other following-described embodiments, expressions of embodiments, examples, methods, etc.

The present invention is useful in combination with a blade only, a blade and a clamp, a shear configuration, or numerous other end-effectors. Examples of ultrasonic surgical instruments are disclosed in U.S. Pat. Nos. 5,322,055 and 5,954,736 and in combination with ultrasonic blades and surgical instruments as, for example, disclosed in U.S. Pat. Nos. 6,309,400 B2, 6,283,981 B1, and 6,325,811 B1 all of which are incorporated in their entirety by reference herein. These references disclose ultrasonic surgical instrument design and blade designs where a longitudinal mode of the blade is excited. Because of asymmetry or asymmetries, these blades exhibit transverse and/or torsional motion where the characteristic "wavelength" of this non-longitudinal motion is less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e. will have at least longitudinal motion along the length extending from its distal end, an antinode of longitudinal motion, to the first nodal position of longitudinal motion that is proximal to the tissue effector portion).

Figure 1:
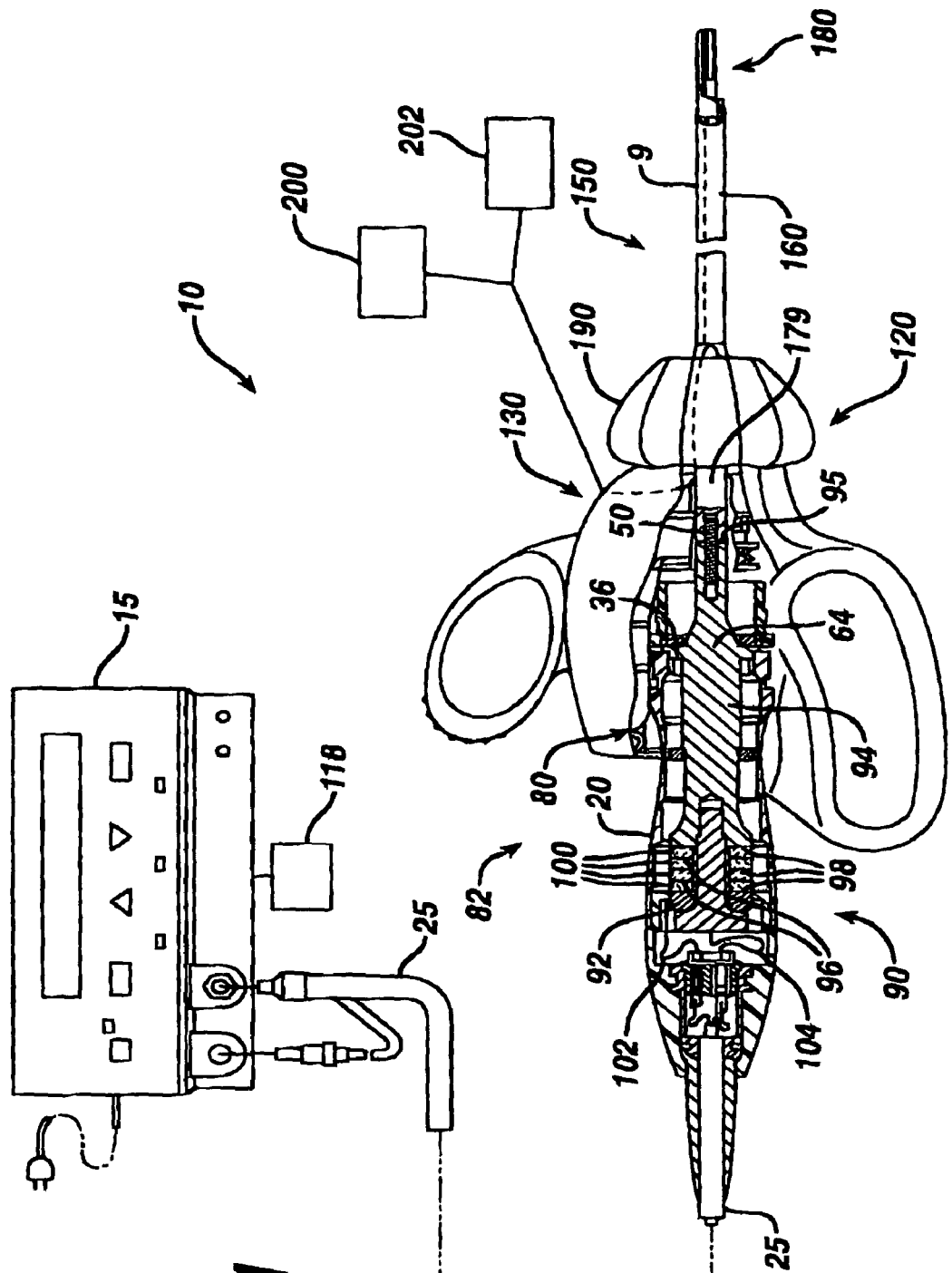
FIG. 1 illustrates an ultrasonic surgical system including an elevation view of an ultrasonic generator, a sectioned plan view of an ultrasonic transducer, and a partially sectioned plan view of a clamp coagulator in accordance with the present invention.

FIG. 1 illustrates ultrasonic system 10 comprising an ultrasonic signal generator 15 with ultrasonic transducer 82, hand piece housing 20, and clamp coagulator 120 in accordance with the present invention. Clamp coagulator 120 may be used for open or laparoscopic surgery. The ultrasonic transducer 82, which is known as a "Langevin stack", generally includes a transduction portion 90, a first resonator or end-bell 92, and a second resonator or fore-bell 94, and ancillary components. The ultrasonic transducer 82 is preferably an integral number of one-half system wavelengths ($n\lambda/2$) in length as will be described in more detail later. An acoustic assembly 80 includes the ultrasonic transducer 82, mount 36, velocity transformer 64 and surface 95.

The distal end of end-bell 92 is connected to the proximal end of transduction portion 90, and the proximal end of fore-bell 94 is connected to the distal end of transduction portion 90. Fore-bell 94 and end-bell 92 have a length determined by a number of variables, including the thickness of the transduction portion 90, the density and modulus of elasticity of the material used to manufacture end-bell 92 and fore-bell 94, and the resonant frequency of the ultrasonic transducer 82. The fore-bell 94 may be tapered inwardly from its proximal end to its distal end to amplify the ultrasonic vibration amplitude as velocity transformer 64, or alternately may have no amplification.

The piezoelectric elements 100 may be fabricated from any suitable material, such as, for example, lead zirconate-titanate, lead meta-niobate, lead titanate, or other piezoelectric crystal material. Each of the positive electrodes 96, negative electrodes 98, and piezoelectric elements 100 has a bore extending through the center. The positive and negative electrodes 96 and 98 are electrically coupled to wires 102 and 104, respectively. Wires 102 and 104 are encased within cable 25 and electrically connectable to ultrasonic signal generator 15 of ultrasonic system 10.

Ultrasonic transducer 82 of the acoustic assembly 80 converts the electrical signal from ultrasonic signal generator 15 into mechanical energy that results in primarily longitudinal vibratory motion of the ultrasonic transducer 82 and an end-effector 180 at ultrasonic frequencies. A suitable generator is available as model number GEN01, from Ethicon Endo-Surgery, Inc., Cincinnati, Ohio. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength ($\lambda/4$).

Wires 102 and 104 transmit the electrical signal from the ultrasonic signal generator 15 to positive electrodes 96 and negative electrodes 98. The piezoelectric elements 100 are energized by an electrical signal supplied from the ultrasonic signal generator 15 in response to a foot switch 118 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing longitudinal waves of ultrasonic energy. The ultrasonic energy is transmitted through the acoustic assembly 80 to the end-effector 180.

In order for the acoustic assembly 80 to deliver energy to end-effector 180, all components of acoustic assembly 80 must be acoustically coupled to the ultrasonically active portions of clamp coagulator 120. The distal end of the ultrasonic transducer 82 may be acoustically coupled at surface 95 to the proximal end of an ultrasonic waveguide 179 by a threaded connection such as stud 50.

The components of the acoustic assembly 80 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 80, and where n is any positive integer. It is also contemplated that the acoustic assembly 80 may incorporate any suitable arrangement of acoustic elements.

The clamp coagulator 120 may include an instrument housing 130, and an elongated member 150. The elongated member 150 can be selectively rotated with respect to the instrument housing 130. Located at the distal end of the outer tube 160 is an end-effector 180 for performing various tasks, such as, for example, grasping tissue, cutting tissue and the like.

Figure 2:
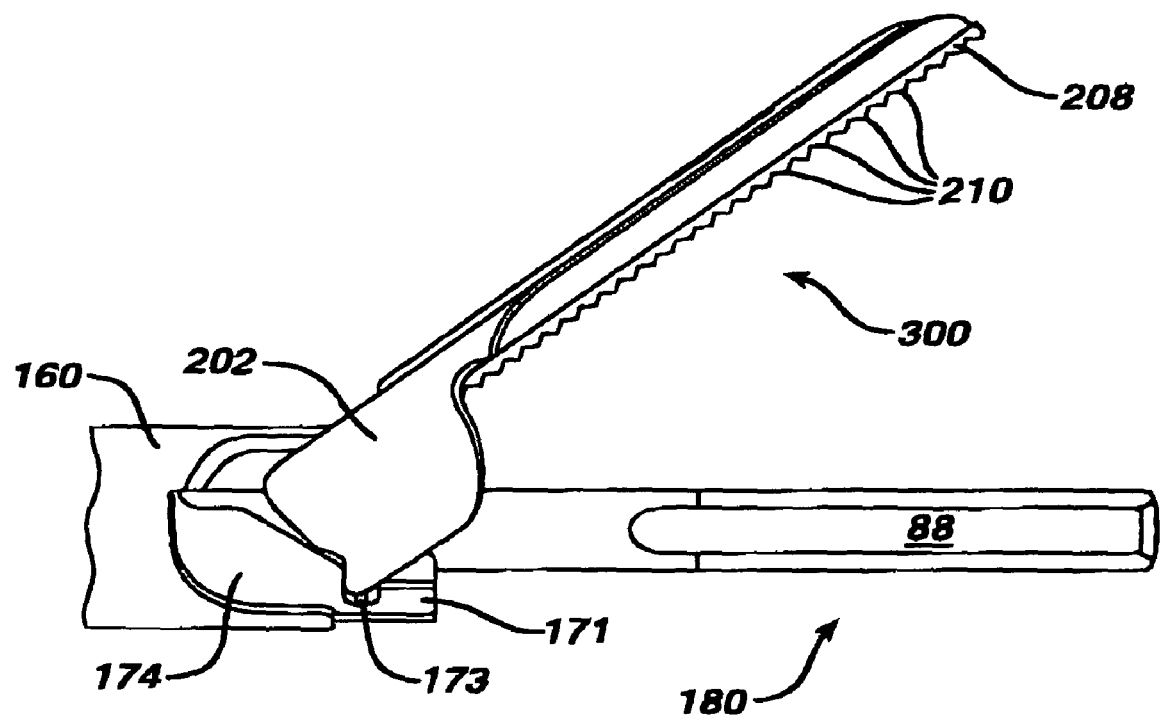
FIG. 2 is a side view of an end-effector of the clamp coagulator with the clamp arm open.
Figure 3A:
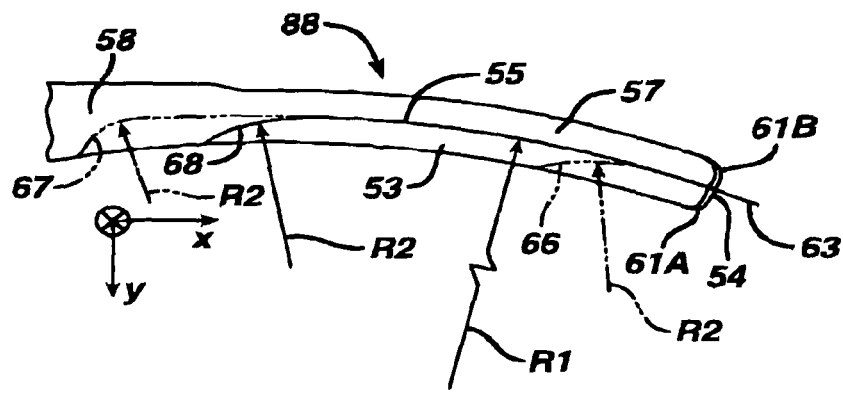
FIG. 3a is a bottom plan view of a blade of the clamp coagulator.
Figure 3B:
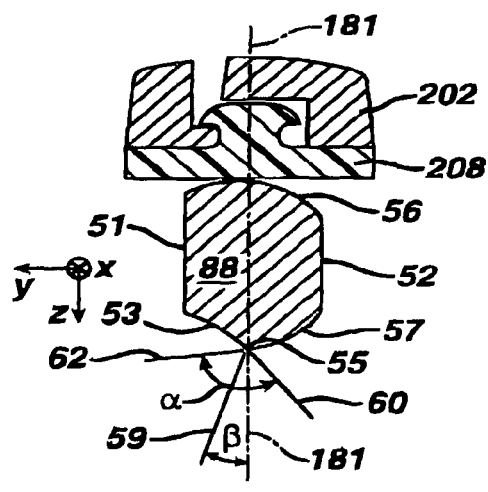
FIG. 3b is a cross-sectional view of a blade of the clamp coagulator.
Figure 3C:
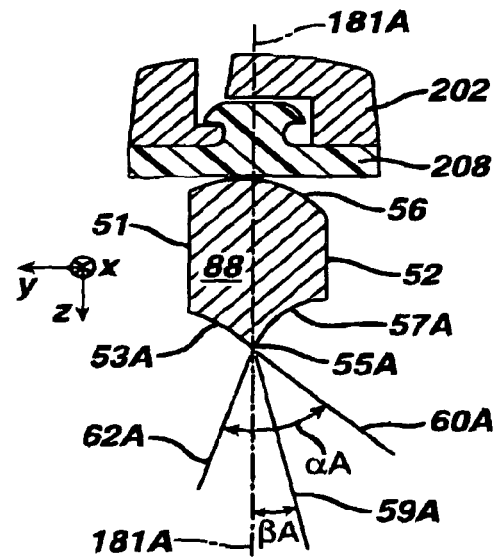
FIG. 3c is a cross-sectional view of an alternate embodiment of a blade of the clamp coagulator.
Figure 4:
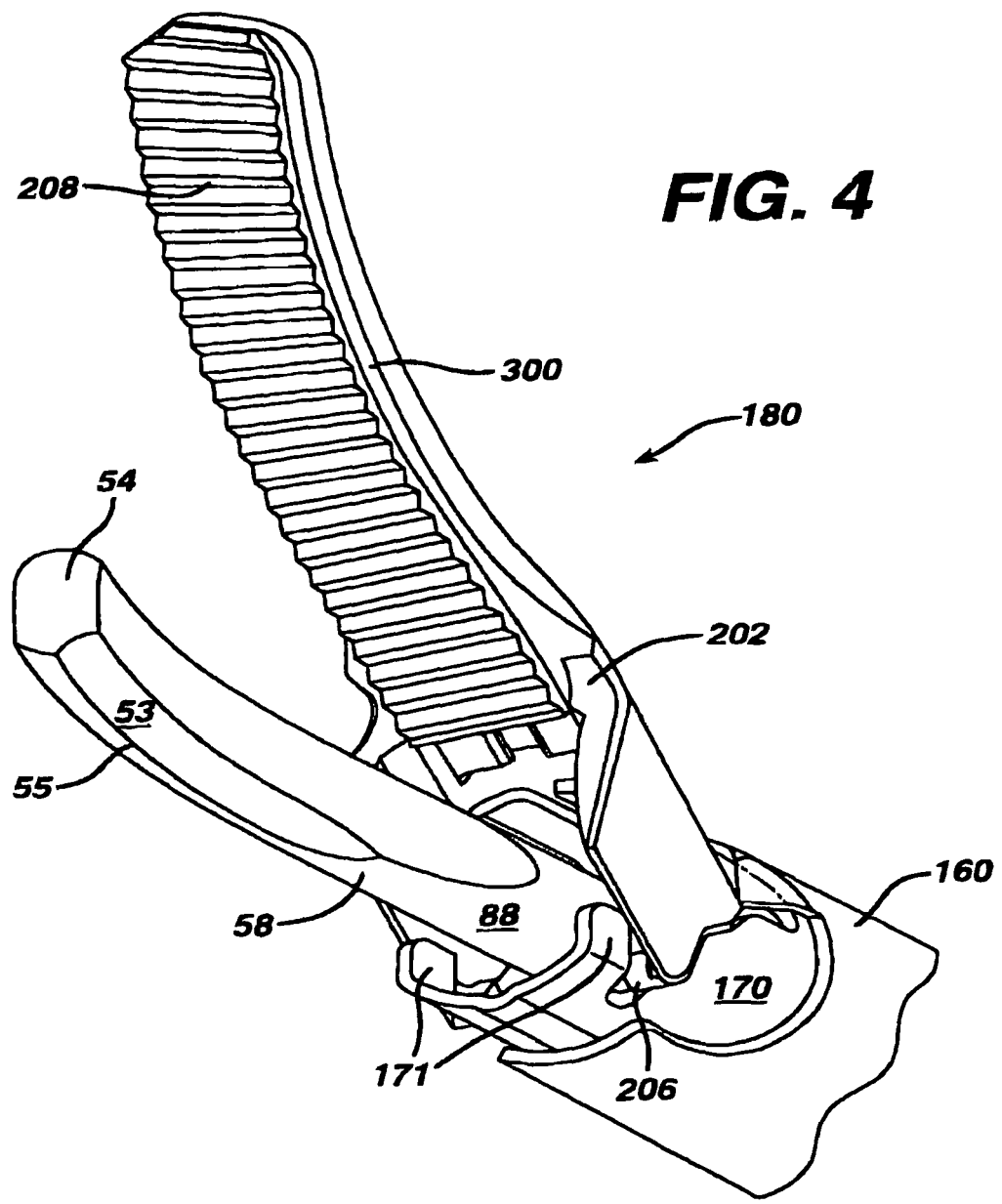
FIG. 4 is a perspective view of an end-effector of the clamp coagulator.

End-effector 180 and its components are shown in greater detail in FIGS. 2 through 4. The end-effector 180 generally includes a non-vibrating clamp arm assembly 300 to, for example, grip tissue or compress tissue against the ultrasonic blade 88. The end-effector 180 is illustrated in FIGS. 2 and 4 in a clamp open position, and clamp arm assembly 300 is preferably pivotally attached to the distal end of the outer tube 160. The clamp arm 202 has tissue pad 208 with serrations 210 attached thereto for squeezing tissue between the ultrasonic blade 88 and clamp arm assembly 300.

The distal end of the tubular member 174 of the inner tube 170 preferably includes a finger or flange 171 that extends therefrom. The flange 171 has an opening 173A and an opening 173B (not shown) to receive the first post 206A and second post 206B of the clamp arm 202. When the inner tube 170 of the elongated member 150 is moved axially, the flange 171 moves forwardly or rearwardly while engaging the first post 206A and second post 206B of the clamp arm assembly 300 to open and close the clamp arm 202.

The ultrasonic waveguide 179 of the elongated member 150 extends through aperture 175 of the inner tube 170. The ultrasonic waveguide 179 is preferably substantially semi-flexible. It will be recognized that the ultrasonic waveguide 179 may be substantially rigid or may be a flexible wire. Ultrasonic vibrations are transmitted along the ultrasonic waveguide 179 in a longitudinal direction to vibrate the ultrasonic blade 88.

The ultrasonic waveguide 179 may, for example, have a length substantially equal to an integral number of one-half system wavelengths ($n\lambda/2$). The ultrasonic waveguide 179 may be preferably fabricated from a solid core shaft constructed out of material that propagates ultrasonic energy efficiently, such as titanium alloy (i.e., Ti-6Al-4V) or an aluminum alloy. The ultrasonic waveguide 179 may also amplify the mechanical vibrations transmitted to the ultrasonic blade 88 as is well known in the art.

The ultrasonic blade 88 may have a length substantially equal to an integral multiple of one-half system wavelengths ($n\lambda/2$). The distal end of ultrasonic blade 88 may be disposed near an antinode in order to provide the maximum longitudinal excursion of the distal end. When the transducer assembly is energized, the distal end of the ultrasonic blade 88 is configured to move in the range of, for example, approximately 10 to 500 microns peak-to-peak, and preferably in the range of about 30 to 150 microns at a predetermined vibrational frequency.

The ultrasonic blade 88 is preferably made from a solid core shaft constructed of material which propagates ultrasonic energy, such as a titanium alloy (i.e., Ti-6Al-4V) or an aluminum alloy and can be of various geometries. As illustrated in FIGS. 3a-c and 4, the geometry of the ultrasonic blade 88 delivers ultrasonic power more uniformly to clamped tissue than predicate devices. The end-effector 180 provides for improved visibility of the blade tip so that a surgeon can verify that the blade 88 extends across the structure being cut or coagulated. This is especially important in verifying margins for large blood vessels. The geometry also provides for improved tissue access by more closely replicating the curvature of biological structures. Blade 88 provides a multitude of edges and surfaces, designed to provide a multitude of tissue effects: clamped coagulation, clamped cutting, grasping, back-cutting, dissection, spot coagulation, tip penetration and tip scoring.

The distal most tip of blade 88 has a surface 54 perpendicular to tangent 63, a line tangent to the curvature at the distal tip. Two fillet-like features 61A and 61B are used to blend surfaces 51, 52 and 54, thus giving a blunt tip that can be utilized for spot coagulation. The top of the blade 88 is radiused and blunt, providing a broad edge, or surface 56, for clamping tissues between it and clamp arm assembly 300. Surface 56 is used for clamped cutting and coagulation as well as manipulating tissues while the blade is inactive.

The bottom surface has a spherical cut 53 that provides a narrow edge, or sharp edge 55, along the bottom of blade 88. The material cut is accomplished by, for example, sweeping a spherical end mill through an arc of radius R1 and then finishing the cut using a second, tighter radius R2 that blends the cut with a bottom surface 58 of the blade 88. Radius R1 is preferably within the range of 0.5 inches to 2 inches, more preferably within the range of 0.9 inches to 1.1 inches, and most preferably about 1.068 inches. Radius R2 is preferably within the range of 0.125 inches to 0.5 inches, and most preferably about 0.25 inches. The second radius R2 and the corresponding blend with the bottom surface 58 of blade 88 diminishes the stress concentrated at the end of the spherical cut relative to stopping the cut without this blend. The sharp edge 55 facilitates dissection and unclamped cutting (back-cutting) through less vascular tissues.

Spherical cut 53 on bottom surface 58 of blade 88 creates sharp edge 55 while removing a minimal amount of material from blade 88. Spherical cut 53 on the bottom of blade 88 creates a sharp edge 55 with an angle of α as described below. This angle α may be similar to predicate shears devices such as, for example, the LCS-K5 manufactured by Ethicon Endo-Surgery, Inc., Cincinnati, Ohio. However blade 88 cuts faster than predicate devices by virtue of the orientation of the angle α with respect to the typical application force. For the predicate shears devices, the edges are symmetric, spanning the application force equally. The edges for the present invention are asymmetric, with the asymmetry of the edges dictating how quickly tissue is separated or cut. The asymmetry is important in that it provides for an effectively sharper edge when ultrasonically activated, without removing a significant volume of material, while maintaining blunt geometry. This asymmetric angle as well as the curvature of the blade act to self tension tissue during back-cutting utilizing a slight hook-like or wedge-like action.

Sharp edge 55 of ultrasonic blade 88 is defined by the intersection of surface 53 and a second surface 57 left after bottom surface 58 has received spherical cut 53. Clamp arm assembly 300 is pivotally mounted on said distal end of outer tube 160 for pivotal movement with respect to ultrasonic blade 88, for clamping tissue between clamp arm assembly 300 and ultrasonic blade 88. Reciprocal movement of inner tube 170 pivots clamp arm assembly 300 through an arc of movement, defining a vertical plane 181. A tangent 60 of spherical cut 53 at sharp edge 55 defines an angle α with a tangent 62 of second surface 57, as illustrated in FIG. 3b. The bisection 59 of angle α preferably does not lie in vertical plane 181, but is offset by an angle β. Preferably the tangent 60 of spherical cut 53 lies within about 5 to 50 degrees of vertical plane 181, and most preferably the tangent of spherical cut 53 lies about 38.8 degrees from vertical plane 181. Preferably angle α is within the range of about 90 to 150 degrees, and most preferably angle α is about 121.6 degrees.

Looking to FIG. 3c, an alternate embodiment illustrated with an asymmetric narrow edge. A tangent 60A of a spherical cut 53A at a sharp edge 55A defines an angle αA with a tangent 62A of a second surface 57A, as illustrated in FIG. 3c. A bisection 59A of angle αA preferably does not lie in a vertical plane 181A, but is offset by an angle βA.

The curved shape of the design of ultrasonic blade 88 also results in a more uniformly distributed energy delivery to tissue as it is clamped against the blade 88. Uniform energy delivery is desired so that a consistent tissue effect (thermal and transection effect) along the length of end-effector 180 is achieved. The distal most 15 millimeters of blade 88 is the working portion, used to achieve a tissue effect. As will be further described below, the displacement vectors for locations along the curved shears blade 88 have directions that, by virtue of the improvements of the present invention over predicate instruments, lie largely in the x-y plane illustrated in FIGS. 3a-c. The motion, therefore, of blade 88 lies within a plane (the x-y plane) that is perpendicular to the direction of the clamping force from clamp arm assembly 300.

Straight symmetric ultrasonic blades in general have tip excursions that lie along the longitudinal axis, designated the x-axis in FIGS. 3a-c. Transverse motion is usually undesirable because it results in undesirable heat generation in inner tube 170. When a functional asymmetry is added to an ultrasonic blade, such as a curved end-effector as described in U.S. patent application Ser. No. 09/106,686 incorporated herein by reference, the functional asymmetry creates an imbalance in the ultrasonic waveguide. If the imbalance is not corrected, then undesirable heat, noise, and compromised tissue effect occur. Although U.S. patent application Ser. No. 09/106,686 teaches how to provide ultrasonic blades that are balanced proximal to the balance asymmetry, the distal portion of the end-effector has an excursion in at least two axes. If the end-effector has a single plane of functional asymmetry, such as a curved end-effector, but the blade is otherwise symmetric, then the excursion will lie in a plane at the distal most end.

It is often desirable to minimize any ultrasonic blade 88 excursion in the z-axis direction. Excursion of ultrasonic blade 88 in the z-axis direction causes system inefficiencies, resulting in undesirable heating, power loss, and possibly noise. Excursion of ultrasonic blade 88 in the z-axis direction at end-effector 180 causes the ultrasonic blade 88 to impact tissue lying between ultrasonic blade 88 and clamp arm assembly 300. It is desirable to limit ultrasonic blade 88 excursion to the x-y plane shown in FIGS. 3a-c. This allows ultrasonic blade 88 to rub tissue lying between ultrasonic blade 88 and clamp arm assembly 300 without impact, which optimizes heating of the tissue, and thus provides optimal coagulation. Minimizing z-axis excursion both proximal to the end-effector 180, and in ultrasonic blade 88, may be accomplished by proper selection of a spherical cut 53.

However, an ultrasonic end-effector 180 with an ultrasonic blade 88 that has multiple functional asymmetries, such as ultrasonic blade 88 as illustrated in FIGS. 3-4, will naturally have a tendency to include tip excursion in all three axes, x, y, and z if not balanced properly. For example, ultrasonic blade 88 as illustrated in FIG. 3a is curved in the y direction at its distal end. This curvature, although balanced proximal to end-effector 180, will cause ultrasonic blade 88 to have excursions in both the x and y directions when activated. Adding spherical cut 53 subsequently adds another level of asymmetry to ultrasonic blade 88, causing tip excursion in all three axes if not corrected, and also causing z-axis imbalances in ultrasonic waveguide 179 which decreases efficiency.

It is possible to minimize z-axis tip excursion proximal to the functional asymmetry, and therefore maximize efficiency with improved tissue effect, by providing a functional asymmetry optimized to minimize z-axis excursion in ultrasonic waveguide 179. As illustrated in FIG. 3, spherical cut 53 may extend proximally into ultrasonic blade 88, from the most distal end, to any position. For example, FIG. 3 illustrates a first position 66, a second position 67, and a third position 68, for spherical cut 53 to extend into ultrasonic blade 88.

Table 1 below describes three possible lengths of spherical cuts 53 for ultrasonic blade 88 illustrated in FIG. 3 as first position 66, second position 67, and third position 68. The rows of Table 1 correspond to the length of cut into the ultrasonic blade 88, and the columns of Table 1 correspond to the balance condition and excursions along each axis for each cut length. It can be appreciated from Table 1 that providing spherical cut 53 to a length corresponding to first position 68 minimizes the z axis excursion proximal to the functional asymmetry. It is preferable to balance ultrasonic blade 88 below 15% z axis excursion proximal to the functional asymmetry and it is most preferable to balance ultrasonic blade 88 below 5% z axis excursion proximal to the functional asymmetry. Preferably clamp coagulator 120 is designed to be balanced when activated in air (loaded only by air), and then balance is verified under other load conditions.

In Table 1, a normalized excursion percentage (% z) in a clamping instrument at the end-effector 88 is calculated by taking the magnitude of the excursion in the direction normal to the clamp arm when the clamp arm is in its fully closed position, and dividing that magnitude by the magnitude of the maximum tip vibration excursion (also called the primary tip vibration excursion), and then multiplying the dividend by one hundred. Primary tip vibration excursion is the magnitude of the major axis of the ellipse or ellipsoid created by a point on the distal most end of ultrasonic blade 88 when the ultrasonic blade 88 is activated. The measurement of excursions is more fully explained in IEC international standard 61847, titled *Measurement and Declaration of the Basic Output Characteristics* of ultrasonic surgical systems, hereby incorporated herein by reference. A normalized excursion percentage (% x, % y, % z) in ultrasonic blade 88 or ultrasonic waveguide 179 is calculated by taking the magnitude of a secondary vibration excursion, and dividing that magnitude by the magnitude of the primary tip vibration excursion, and then multiplying the dividend by one hundred. Secondary tip vibration excursion is the magnitude of a minor axis, or other arbitrary axis, of the ellipse or ellipsoid created by a point on the distal most end of ultrasonic blade 88 when the ultrasonic blade 88 is activated.

TABLE 1

Three possible lengths to provide a range of balances for a 0.946 inch long blade with a radius of R1 manufactured from Ti6AI4V with the blade including a functional asymmetry.

| | % x at distal end of blade 88 | % y at distal end of blade 88 | % z at distal end of blade 88 | % z proximal to blade 88 |
|---|---|---|---|---|
| Cut Length = 12.8 mm, Location at first position 68 | 71.83 | 69.47 | 4.15 | 0.40 |
| Cut Length = 14.8 mm Location at second position 67 | 72.49 | 68.87 | 1.60 | 12.43 |
| Cut Length = 8.2 mm, Location at third position 66 | 74.54 | 66.03 | 9.21 | 8.25 |

Figure 5:
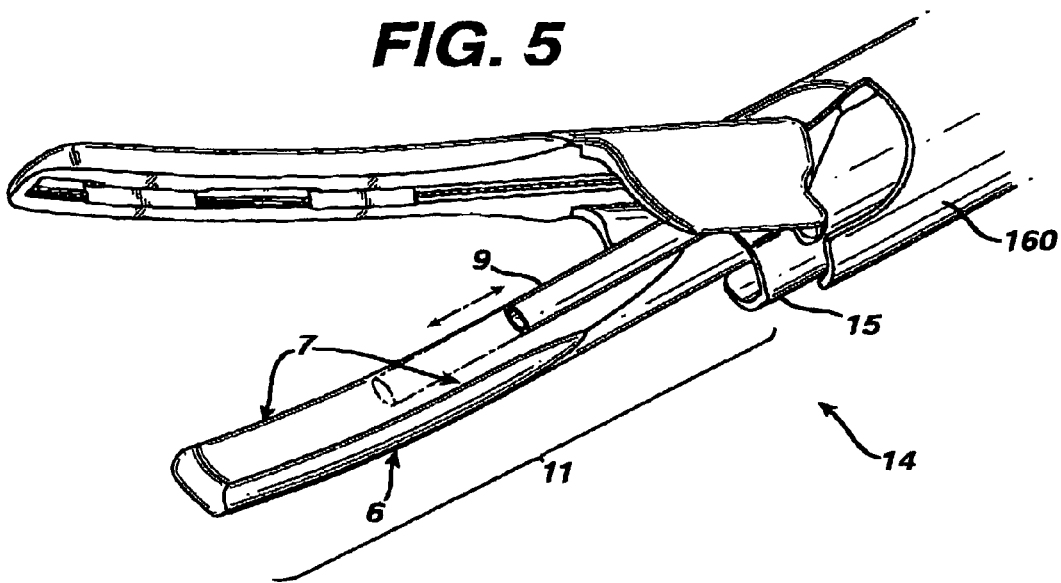
FIG. 5 is a perspective view of one embodiment of a fluid management lumen for use with a clamp and curved blade ultrasonic end effector.

FIG. 5 discloses the ultrasonic end effector 180, featuring a lumen 9, which permits irrigation/suction during surgical procedures. Lumen 9 may consist of a single tube with a single lumen, several tubes or a single tube with multiple lumens. Additionally, the lumen or lumens may have cross-sectional shapes selected from many manufacturable designs including, but not limited to, round, half round, partial round, rectangular, pyramidal, etc. Lumen 9 may be extendable/retractable with respect to blade 6. In the preferred embodiment, lumen 9 is extended or retracted to a nodal (longitudinal, transverse, or torsional-mode or motion) position 7 or any other desirable position along a representative blade 6. There are many variations in blade 6 shape and length such as a spoon shape, a blade 6 with a dramatic curve, a blade 6 with a flat curve, etc. These embodiments of ultrasonic surgical device 14 alter the location of the nodal positions 7, at times creating several nodal locations 7 along the blade 6. These particular examples are designed to be excited at a frequency corresponding to a longitudinal mode, but they will have non-longitudinal motion (i.e. transverse motion) occurring in a wave pattern with associated non-longitudinal nodes present at one or more location along the tissue effecting portion. The lumen 9 is extendable/retractable to allow the terminus of lumen 9 to be positioned at one of the transverse nodal positions 7. The lumen 9 is retractable/extendable by several means, including manual extension, gear extension, trigger extension and by other means of mechanical actuation that may be located at the proximal end of surgical device 14, as is well known to those skilled in the design of medical instruments. The method of creating suction/irrigation through lumen 9 may be done through a variety of means such as by attaching lumen 9 to a stand alone suction/irrigation module, tower mounted suction 200 and/or irrigation 202 modules (FIG. 1), or an integrated ultrasonic generator/suction/irrigation module in the operating room. It may also be advantageous to integrate suction/irrigation controls (i.e. trumpet valves, etc.) and a means for selecting either suction or irrigation within the device handle.

In the preferred embodiment, lumen 9 is located on the concave side of blade 6, though placement of the lumen 9 around the blade may vary depending on the needs of the physician, blade shape and/or acoustic characteristics. Lumen 9 may be made of numerous materials, though the material of the lumen 9 in the preferred embodiment is polymeric in nature. Examples of lumen materials include but are not limited to the following: FEP (fluorinated ethylene-propylene), PTFE (polytetrafluoroethylene), polyimide, nylon, PET (polyethylene terephthalate), PFA (perfluoroalkoxy), PVDA (polyvinylidene acetate), ETFE (ethylene tetrofluoroethylene), and polyethylene (high and low density). In the preferred embodiment, lumen 9 is fitted down an inner actuating tube 15 alongside the blade, held away from the blade by a series of silastic or polymeric stand-offs (not shown). Other embodiments may include the lumen 9 being fit between the blade and a tube (in the case of a blade-only configuration) an inner 15 and outer tube 160 (in the case of either shears or blade-only configurations), integrated into the tube, or alternatively, along the outside of a single support outer tube 160. The lumen 9 is also extendable/retractable along the entire length 11 of the blade 6, though the preferred location of the lumen 9 termination during surgical procedures is at or just proximal to a nodal position 7 for suction removal of fluids and/or debris, beyond the distal terminus of the end-effector for irrigation, and at the proximal terminus of the end-effector for suction removal of vapor and/or aerosol.

Figure 6A:
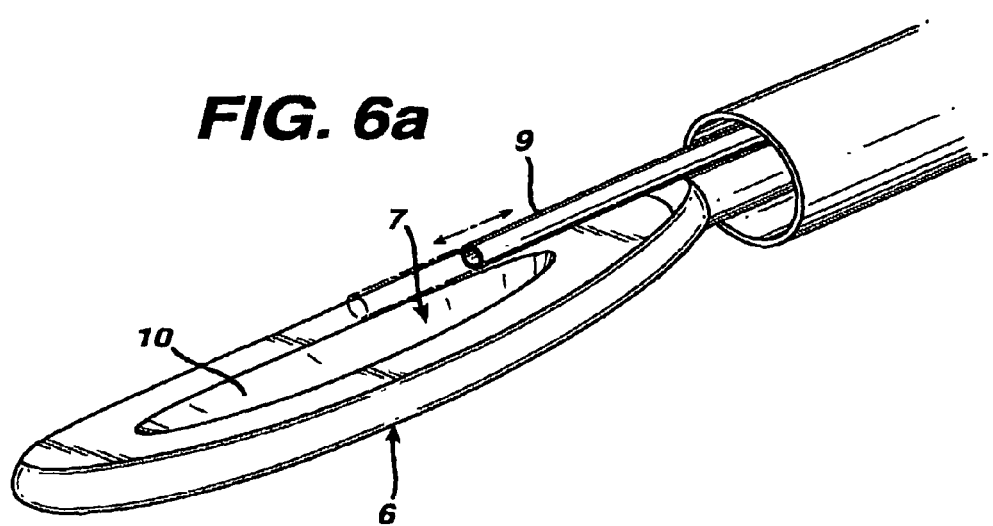
FIGS. 6a-c are perspective views of a fluid management lumen in combination with alternate embodiments of ultrasonic blade end effectors.
Figure 6B:
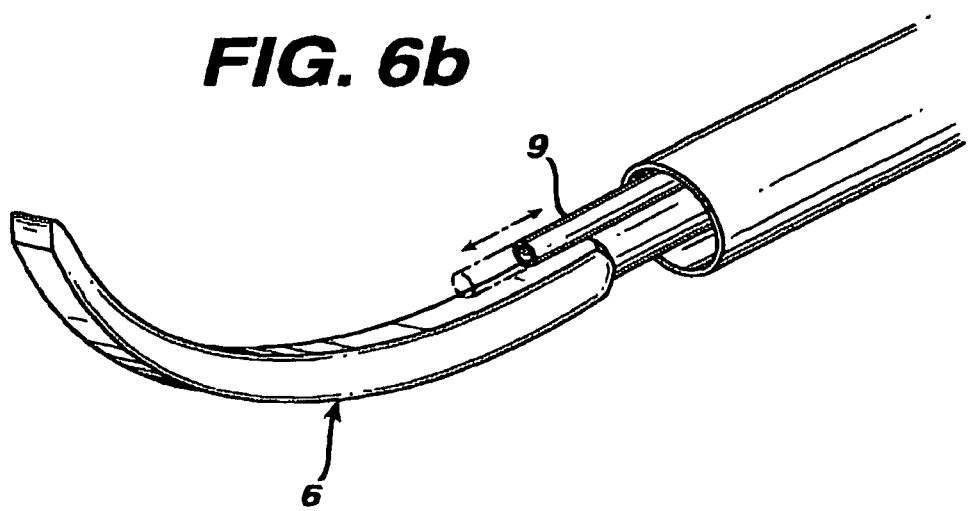
Figure 6C:
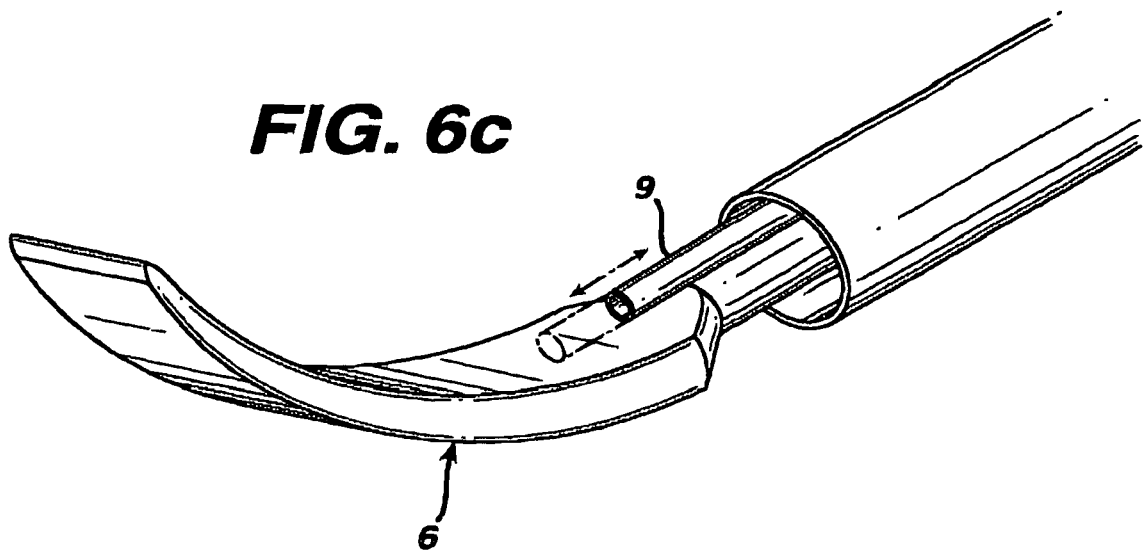

FIGS. 6*a-c* disclose several alternate embodiments of the blade 6. FIG. 6*a* discloses a blade 6 having a spoon shape. The spoon shape of blade 6 creates a concave surface or channel 110 within the curvature of blade 6. Channel 110 allows for particles to collect at a nodal position 7 preventing the particles from escaping from the blade 6. The lumen 9, preferably located at or just proximal to a transverse motion nodal position 7, suctions the particles out of channel 10. FIGS. 2*b* and 2*c* illustrate a dramatic curve of blade 6 and a wide, spatula-like blade 6, respectively. Blade 6 may also be made out of numerous materials such as, but not limited to, titanium, aluminum, Stellite or ceramics.

Figure 7A:
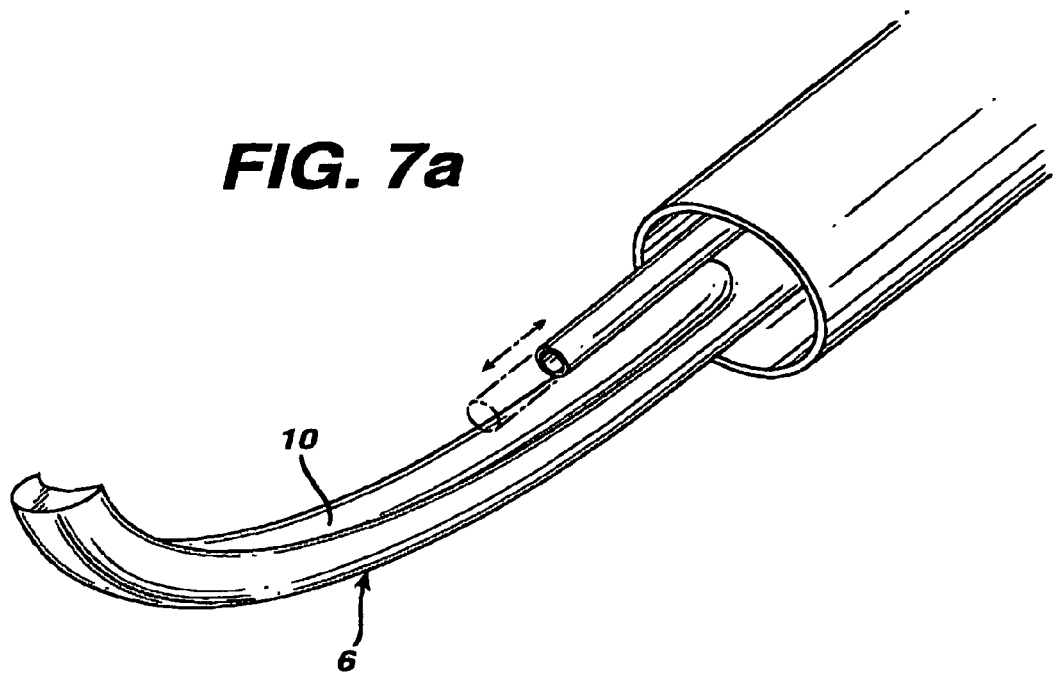
FIGS. 7a-b are perspective views of a fluid management lumen in combination with ultrasonic blade end effectors having channels.
Figure 7B:
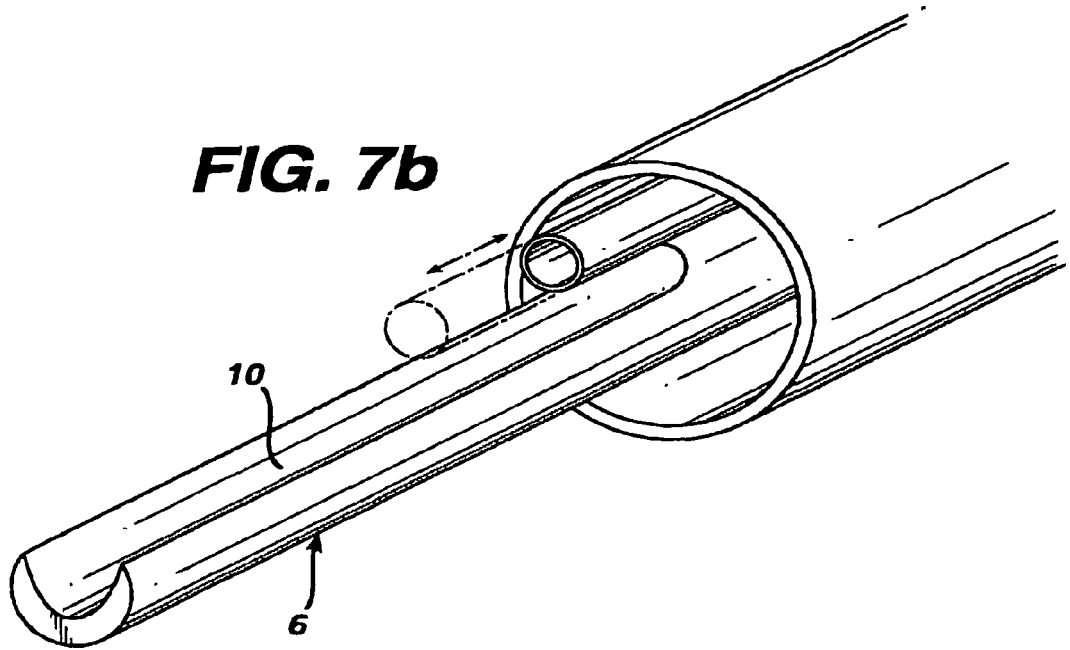

FIGS. 7*a* and *b* illustrates two alternate embodiments for a cavity or channel 110, which may or may not be present in ultrasonic surgical instrument 14 depending on the needs of the physician. FIG. 7*a* discloses a curved blade 6 featuring a curved channel 110 that terminates at the distal end of blade 6. FIG. 7b illustrates a second embodiment of channel 110 incorporated into a straight blade 6. Channel 110 may have numerous embodiments such as a spoon-like appearance, a curved shape, a straight shape, sharp knife edges, etc. Channel 110 may also have a wide variety of lengths, widths and depths from blade to blade or channel 110 may have varying widths and depths along the length of a blade. Further, channel 110 may take on other forms such as a V-groove or square channel. This channel may be designed such that it provides support or constraint for the lumen/lumens.

Figure 8:
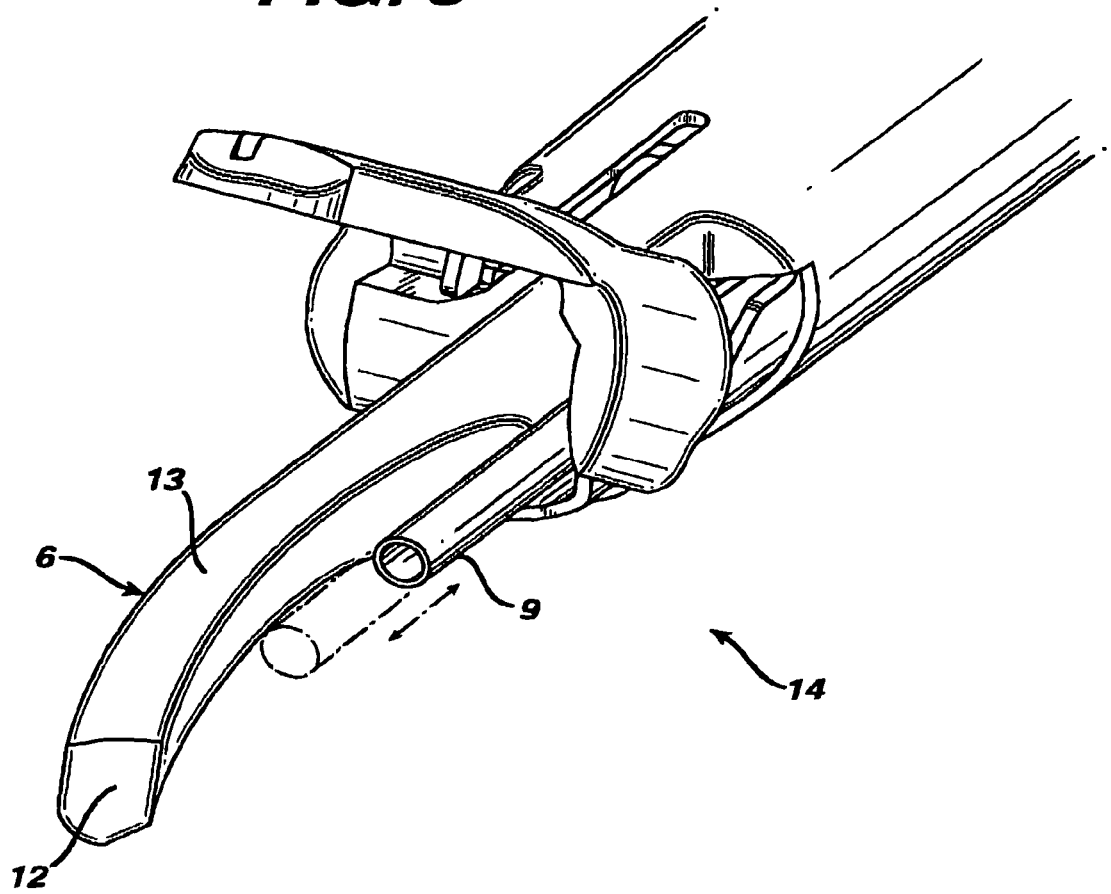
FIG. 8 is a perspective view of an alternate embodiment of a blade and clamp in combination with a fluid management lumen.
Figure 9A:
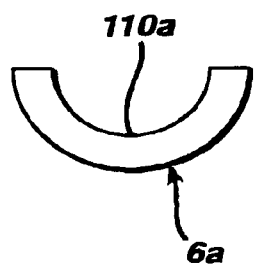
FIG. 9a-e are elevation views of alternate ultrasonic blade designs for use with in combination with a fluid management lumen.
Figure 9B:
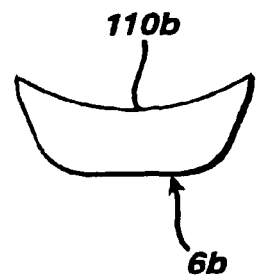
Figure 9C:
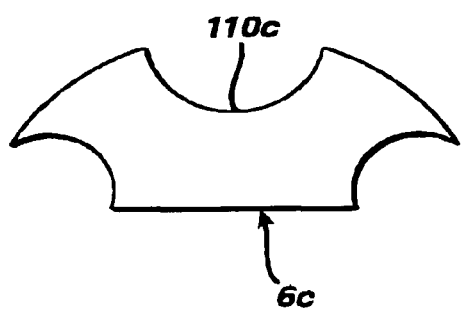
Figure 9D:
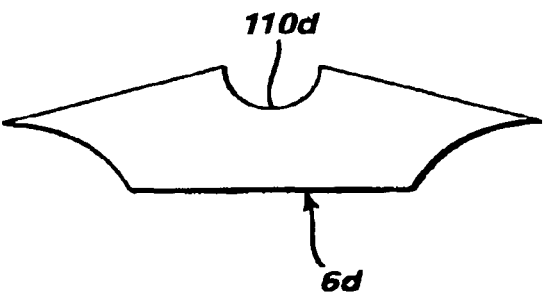
Figure 9E:
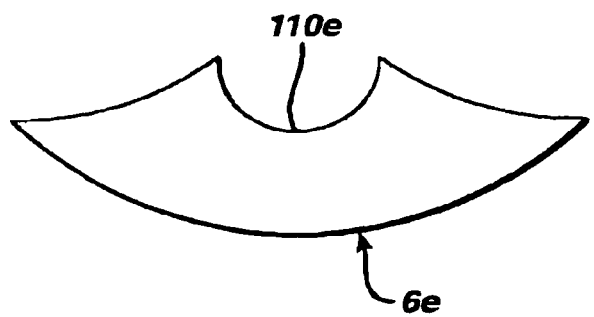

FIG. 8 illustrates one embodiment of an ultrasonic shears device 14 in which the lumen 9 is present. In this alternate embodiment, the area for spot coagulation/cavitation 12 is disclosed, as well as the preferred area for a possible clamping surface 13. If used with a clamping device, clamping surface 13 is the preferred area for clamp coagulation and cutting, though the area is not limited to this position. FIG. 8 also illustrates the possible distal/proximal extension/retraction movements lumen 9 may make in relation to the blade 6.

FIGS. 9a-e discloses numerous cross-sectional embodiments of the blade 6 and the channel 110a-e.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

We claim:

1. An ultrasonic surgical instrument comprising:
   an ultrasonic transducer configured for generating ultrasonic energy and having a proximal end and a distal end;
   an ultrasonic waveguide for transmitting ultrasonic energy and connected to the distal end of the ultrasonic transducer, and having an ultrasonically actuated blade defining an asymmetric portion and positioned at the distal end of the waveguide; and
   a lumen having an end positioned in an overlapping relationship with at least a portion of the asymmetric portion of the blade.

2. The ultrasonic surgical instrument of claim 1, wherein the lumen provides suction to remove fluid, debris, or vapors from a surgical field.

3. The ultrasonic surgical instrument of claim 1, wherein the lumen provides irrigation fluid to a surgical site.

4. The ultrasonic surgical instrument of claim 1, wherein the blade is designed to vibrate in a longitudinal motion coupled with either a transverse or torsional motion.

5. The ultrasonic surgical instrument of claim 4, wherein the lumen is fixed in a position adjacent to a transverse or torsional node.

6. The ultrasonic surgical instrument of claim 4, wherein the lumen is movable to a position adjacent to a transverse or torsional node.

7. The ultrasonic surgical instrument of claim 5, wherein the transverse or torsional node facilitate debris or fluid removal in conjunction with suction.

8. The ultrasonic surgical instrument of claim 1, wherein the lumen is movable radially with respect to the blade.

9. The ultrasonic surgical instrument of claim 1, wherein the proximal end of the surgical instrument incorporates controls for suction and or irrigation functionality.

10. The ultrasonic surgical instrument of claim 1, wherein the blade defines a channel.

11. The ultrasonic surgical instrument of claim 10, wherein the channel directs debris and/or fluids toward the lumen for removal with suction.

12. The ultrasonic surgical instrument of claim 10, wherein the channel directs irrigation fluid from the lumen to the surgical site.

13. An ultrasonic surgical instrument comprising:
    a housing
    an ultrasonic transducer contained at least in part within the housing and configured for generating ultrasonic energy and having a proximal end and a distal end;
    an outer tube having a proximal end joined to the housing, and a distal end;
    an ultrasonic waveguide for transmitting ultrasonic energy and connected to the distal end of the ultrasonic transducer and positioned within the outer tubing, and having
    an ultrasonically actuated blade defining a portion symmetric in at least one plane positioned at the distal end of the waveguide; and
    at least one lumen positioned within the outer tube and in an overlapping relationship with symmetric portion of the blade.

14. The ultrasonic surgical instrument of claim 13, wherein the lumen provides suction to remove fluid, debris, or vapors from a surgical field.

15. The ultrasonic surgical instrument of claim 13, wherein the lumen provides irrigation fluid to a surgical site.

16. The ultrasonic surgical instrument of claim 13, wherein the lumen is moveable.

17. The ultrasonic surgical instrument of claim 13, wherein the blade is designed to vibrate in a longitudinal motion coupled with either a transverse or torsional motion.

18. An ultrasonic surgical instrument comprising:
    an ultrasonic transducer contained at least in part within the housing and configured for generating ultrasonic energy and having a proximal end and a distal end;
    an outer tube;
    an ultrasonic waveguide for transmitting ultrasonic energy and connected to the distal end of the ultrasonic transducer and positioned within the outer tube, and having
    an ultrasonically actuated blade defining an asymmetric portion and positioned at the distal end of the waveguide and extending distally from the outer tube distal end; and
    a lumen positioned within the outer tubing and having an end positioned in an overlapping relationship with at least a portion of the asymmetric portion of the blade.

* * * * *